United States Patent
Tsutsui et al.

(10) Patent No.: US 6,204,422 B1
(45) Date of Patent: Mar. 20, 2001

(54) PROCESS FOR PRODUCING DIALKLYLNAPHTHALENES

(75) Inventors: Toshio Tsutsui; Takumi Sasaki, both of Chuo-ku; Yoshitaka Satou, Sodegaura; Osamu Kubota, Sodegaura; Shinichi Okada, Sodegaura; Masaki Fujii, Chuo-ku, all of (JP)

(73) Assignee: Fuji Oil Company, Ltd., Tokyo (JP)

( * ) Notice: Subject to any disclaimer, the term of this patent is extended or adjusted under 35 U.S.C. 154(b) by 0 days.

(21) Appl. No.: 09/185,727

(22) Filed: Nov. 4, 1998

(30) Foreign Application Priority Data

Nov. 5, 1997 (JP) .................................... 9-302736

(51) Int. Cl.$^7$ ................. C07C 2/66; C07C 4/12
(52) U.S. Cl. .................. 585/321; 525/319; 525/320; 525/323; 525/485; 525/486; 525/488
(58) Field of Search ................... 585/319, 320, 585/321, 323, 485, 486, 488

(56) References Cited

U.S. PATENT DOCUMENTS 5,053,574 * 10/1991 Tsutsui et al. ............... 585/488
6,018,086 * 1/2000 Motoyuki et al. ............ 585/323

* cited by examiner

*Primary Examiner*—Walter D. Griffin
(74) *Attorney, Agent, or Firm*—Wenderoth, Lind & Ponack, L.L.P.

(57) ABSTRACT

A rational technical process for producing dialkylnaphthalenes from petroleum-derived starting materials which exist in abundance is established. The process for producing dialkylnaphthalenes contains the steps (1), (2), (3), and (4): (1) $1^{st}$ step which is for catalytically hydrodealkylating a stock oil containing a substantial amount of naphthalene and/or alkylnapthalenes, separating a product oil form a product gas, and separating and recovering a fraction composed mainly of naphthalene and/or methylnaphthalene from the product oil; (2) $2^{nd}$ step which is for catalytically alkylating or catalytically transalkylating the fraction, recovered in the $1^{st}$ step, composed mainly of naphthalene and/or methylnaphthalene directly without pretreatment for purification, with an alkylating agent or transalkylating agent to prepare alkylnaphthalenes; (3) $3^{rd}$ step which is for separating and recovering dialkylnaphthalenes from the alkylnaphthalenes obtained in the $2^{nd}$ step; and (4) $4^{th}$ step which is for returning at least a part of the residual fraction, after the separation and recovery of dialkylnaphthalenes in the $3^{rd}$ step, as at least a part of the stock oil in the $1^{st}$ step and/or at least part of the alkylating agent or transalkylating agent in the $2^{nd}$ step to the corresponding step.

9 Claims, 1 Drawing Sheet

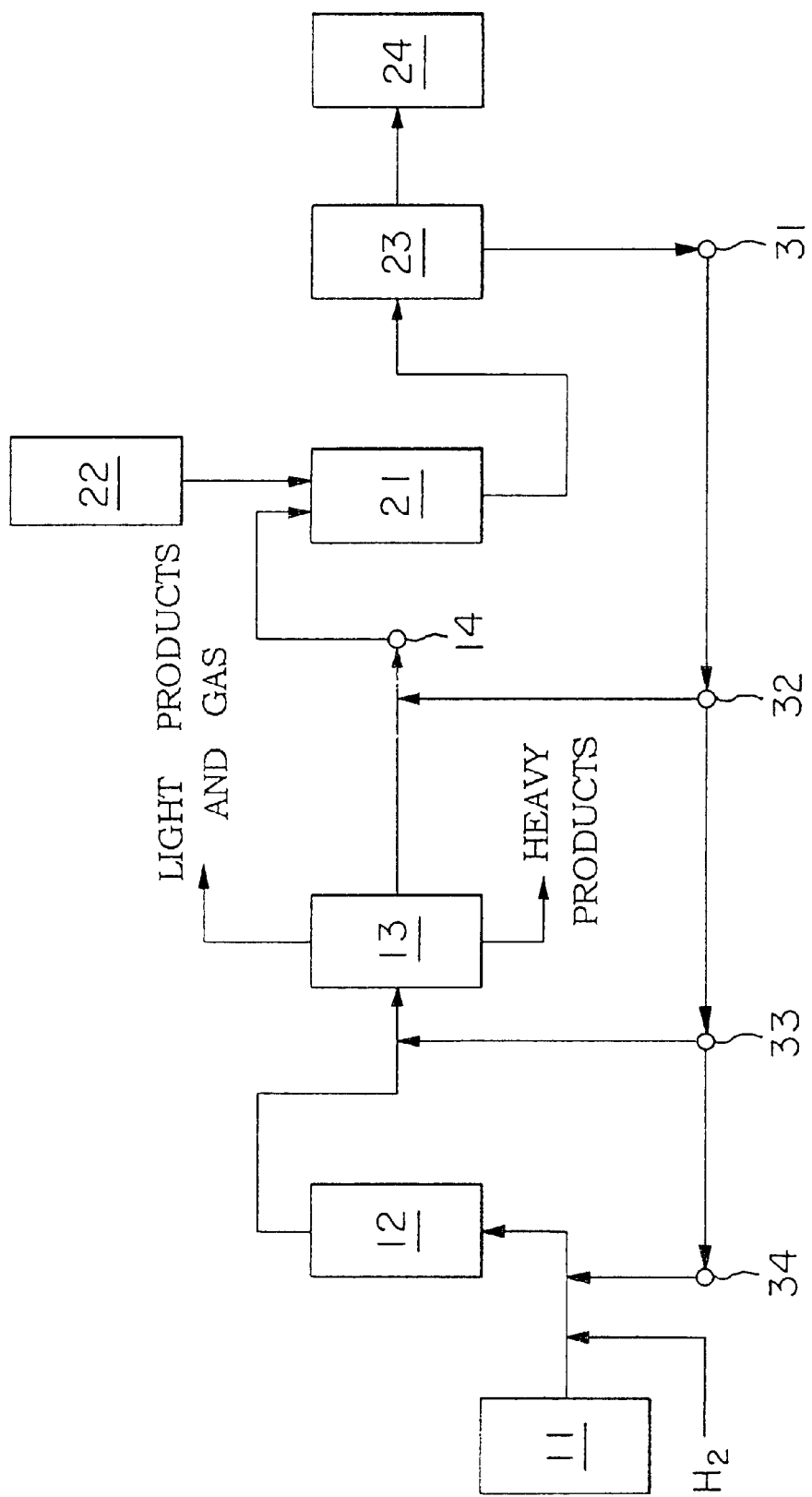

PROCESS FOR PRODUCING DIALKLYLNAPHTHALENES

DETAILED DESCRIPTION OF THE INVENTION

TECHNICAL FIELD OF INVENTION

BACKGROUND OF INVENTION

This invention relates to a process for producing dialkylnaphthalenes. More particularly, this invention relates to a process for producing high-purity diallylnaphthalenes from stock oils containing a substantial amount of naphthalene and/or alkylnaphthalenes, preferably for producing high-purity 2,6-dialkylnaphthalenes, in high yields from light cycle oils produced by catalytic cracking of petroleum.

PRIOR ART

In recent years, attention has been drawn to dialkylnaphthalenes as precursors of monomers for high performance polymers. In particular, 2,6-dialkylnaphthalenes are very important compounds as precursors of monomers for synthesis of polyethylene naphthalate (PEN), which have received attention as engineering plastics required to have a high level of mechanical properties, heat-resistance, stability against chemicals, and electrical and optical properties. They are also important as precursors of monomers for synthesis of fully aromatic liquid crystal polymers which have recently attracted special attention. Under these circumstances, supply of high-purity dialkylnaphthalenes, especially 2,6-diallylnaphthalenes, at low cost has been required in various industries.

Dialkylnaphthalenes are contained in coal tar and petroleum stock oils. These stock oils, however, contain, besides dialkylnaphthalenes, a large quantity of other components and impurities. Therefore, separation of dialkylnaphthalenes directly therefrom would result in low yields and high cost, and, in addition, would not provide high-purity dialkylnaphthalenes suitable for use in subsequent chemical synthesis without difficulty.

Further, in stock oils, a variety of hydrocarbon compounds having boiling points close to dialkylnaphthalenes are present. Therefore, selectively separating and extracting dialkylnaphthalenes alone has been technically and economically difficult.

The coal tar as the starting material is typically a by-product of blast furnace coke production in steelmaking industry. Adoption of advanced technology in steelmaking would lead to markedly reduced production of coal tar in the future. For this reason, supply of stock oils, alternative to the coal tar, would be increasingly required which are easily available and can be supplied at low cost.

On the other hand, dialkylnaphthalenes may be produced also by alkylation of naphthalene or monoalkylnaphthalenes. Naphthalene or monoalkylnaphthalenes as a starting material, particularly naphthalene or methylnaphthalene commonly used in industry, above all, β-methylnaphthalene, is mainly separated from coal tar. These naphthalene and monoalkylnaphthalenes separated from the coal tar contain a large quantity of impurities such as sulfur compounds and nitrogen compounds. Therefore, pretreatments, such as hydrodesulfurization and hydrodenitrogenation, should generally have been carried out to reduce the deactivation of catalysts caused by the impurities and to prevent the formation of alkylated compounds of the impurities. Disadvantageously, however, these pretreatments merely make the, stock oil alkylation process complicate, increase the cost, and, furthermore, cause yield loss due to hydrogenation of naphthalene ring.

Therefore, development of methods for efficiently synthesizing dialkylnaphthalenes, especially 2,6-dialkylnaphthalenes, above all, 2,6-dimethylnaphthalene, 2,6-isopropylmethylnaphthalene, and 2,6-diisopropylnaphthalene by alkylation of naphthalene or methylnaphthalene, especially β-methylnaphthalene, have been desired in industry. The technology, however, has not been satisfactorily established yet.

PROBLEMS TO BE SOLVED BY THE INVENTION

It is a general object of this invention to solve the above problems and to provide a rational technical process for producing dialkylnaphthalenes, especially 2,6-dialkylnaphthalenes, from petroleum stock oils which exist in abundance. It is a more specific object of this invention to establish a production process which has been enhanced in rationality of process and heat balance economics in the whole production process through effective utilization of naphthalene and/or alkylnaphthalenes contained in a large quantity in petroleum stock oils and, in a preferred embodiment, through the removal of catalytic poisons in the alkylation step, and consequently to provide a process for easily producing high-purity dialkylnaphthalenes in high yields at low cost.

MEANS FOR SOLVING THE PROBLEMS OF THE INVENTION

SUMMARY OF THE INVENTION

SUBJECT MATTER

The above objects can be attained by the following present invention.

Namely, the process for producing dialkylnaphthalenes according to this invention comprises the following steps:

(1) 1st step the step of catalytically hydrodealkylating a stock oil containing a substantial amount of naphthalene and/or alkylnaphthalenes, separating a product oil from a product gas, and separating and recovering a fraction composed mainly of naphthalene and/or methylnaphthalene from the product oil;

(2) 2nd step the step of catalytically alkylating or catalytically transalkylating the fraction, recovered in the 1st step, composed mainly of naphthalene and/or methylnaphthalene directly without pretreatment for purification, with an alkylating agent or a transalkylating agent to prepare alkylnaphthalenes;

(3) 3rd step the step of separating and recovering dialkylnaphthalenes from the alkylnaphthalenes obtained in the 2nd step; and (4) 4th step the step of returning at least a part of the residual fraction, after the separation and recover of dialkylnaphthalenes in the 3rd step, as at least a part of the stock oil in the 1st step and/or at least a part of the alkylating agent or transalkylating agent in the 2nd step to the corresponding step.

EFFECT

The process for producing dialkylnaphthalenes according to this invention, comprising the 1st step of hydrodealkylating a stock oil, the 2nd step of directly alkylating (the term "alkylating" used herein including "transalkylating") naphthalene and/or methylnaphthalene produced in the 1st step, the 3rd step of separating and recovering dialkylnaphthalenes from alkylnaphthalenes produced by the alkylation in the 2nd step, and the 4th step of returning the residual fraction, after the separation and recovery of the dialkylnaphthalenes, to the 1st step and/or the 2nd step, can realize the production of dialkylnaphthalenes in an economical and rational manner and can solve various problems involved in the prior art.

Namely, the process for producing dialkylnaphthalenes according to this invention has the following advantages over the process where hydrodealkylation and alkylation are separately conducted. According to the process of this invention, the utilization of alkylnaphthalenes contained in the stock oil can be increased because alkylnaphthalenes other than dialkylnaphthalenes as the target products, that is, by-products, can be reutilized as starting materials. Further, since the high temperature stream as such can be transferred to the next step, the number of process equipments, such as distillation column and heat-exchanger necessary in each step, can be reduced, so that the utilities consumption for heating up the feed stream and cooling down the product can be markedly reduced.

Furthermore, according to the hydrodealkylation step) in the process according to this invention, a hydrodealkylation catalyst having both hydrodesulfurization activity and hydrodenitrogenation activity is preferably used. This permits the hydrodesulfurization reaction and the hydrodenitrogenation reaction to satisfactorily proceed to produce hydrogen sulfide and ammonia which are then separated from the product oil by gas-liquid separation. Therefore, the poisoning of catalyst in the alkylation step can be prevented without provision of an additional desulfurization or denitrogenation step before the alkylation step.

Thus, according to the process of this invention, the alkylation can be advantageously carried out with high selectivity in high yields.

BRIEF DESCRIPTION OF THE DRAWING

The FIGURE is a flowchart of the production process according to this invention.

DESCRIPTION OF REFERENCE NUMERALS

11 Stock oil feeder
12 Hydrodealkylation reactor
13 Separator for hydrodealkylation products
14 Pump
21 Alkylation or transalkylation reactor
22 Feeder for alkylating agent or transalkylating agent
23 Separator for alkylation or transalkylation products
24 Product receiver
31 Pump
32 Pump
33 Pump
34 Pump

DETAILED DESCRIPTION OF THE INVENTION

The process for producing dialkylnaphthalenes according to this invention typically comprises the 1st step of hydrodealkylating a stock oil and recovering the hydrodealkylation product, the 2nd step of alkylating naphthalene and/or others produced in the 1st step to produce alkylnaphthalenes, the 3rd step of separating and recovering the alkylnaphthalenes from the alkylnaphthalenes produced in the 2nd step, and the 4th step of returning by-products in the 3rd step to the 1st step and/or the 2nd step.

1st Step of this Invention

Reactor

The reactor used in the 1st step may be of any type of a fixed bed, a moving bed, and a fluidized bed. Among the above types, the fluidized bed reactor is particularly preferred. This is because, by virtue of high heat-transporting effect and in its turn holding of homogeneous temperature distribution, even an exothermic reaction, such as hydrodealkylation, can be carried out easily and smoothly, and the removal of deactivated catalyst and the supply of regenerated or fresh catalyst can be continuously carried out.

In the case of the fluidized bed system, a method is preferably used in which the catalyst is circulated through a plurality of fluidized beds respectively constituting a reactor (s) and a regenerator(s). In the fluidized bed system, any of a dense bed method and a riser method may be used.

<STOCK OIL>

Any stock oil may be used in the 1st step, so far as it contains a substantial amount of naphthalene and/or alkyl-naphthalenes. In general, however, such oils as coal tar, coal liquefied oil, cracked or reformed oil fractions of petroleum and/or petroleum refining products, such as cracked and/or reformed oil fractions produced by thermal cracking, naphtha cracking, catalytic cracking, catalytic reforming, coking, decarbonizing, visbreaking, or ethylene production process, are used. The stock oil, however, is not limited to the above oils or the above fractions produced by the above processes and may be a mixture of one or more of such oils.

Among the above cracked or reformed oil fractions, those having a boiling point range of 170 to 300° C., more preferably 200 to 290° C., still more preferably 210 to 280° C., are particularly preferred as the stock oil in the invention. Most preferred are light cycle oil fractions of catalytic cracking of petroleum with a boiling point range of 210 to 280° C.

These stock oils may contain impurities, for example, sulfur-containing compounds, such as benzothiophenes, nitrogen-containing compounds, such as quinoline and indole compounds, and oxygen-containing compounds, such as phenol, benzofuran, and dibenzofuran compounds.

Further, at least a portion of the residual fraction after the separation and recovery of dialkylnaphthalenes in the 3rd step may also be used as the stock oil.

<HYDRODEALKYLATION CATALYST>

Any catalyst may be used in the 1st step so far as the catalyst has hydrodealkylation activity. Typical catalysts usable in the 1st step are such that an active metal component described below is supported on a material having a porous structure and a desired other component(s) is optionally incorporated.

Active metal components usable herein include, but are not limited to, metals, such as vanadium (V), molybdenum (Mo), chromium (Cr), cobalt (Co), nickel (Ni), platinum (Pt), rhodium (Rh), and iridium (Ir), and compounds of these metals, such as oxides or sulfides of these metals. They may be used alone or as a mixture of two or more.

The concentration of the active metal component in terms of metal used in the catalyst is preferably 0.1 to 30 wt %, more preferably 0.2 to 20 wt %, most preferably 0.3 to 15 wt %.

Typical examples of materials having a porous structure include, but are not limited to, alumina, silica, silica-alumina, and kaolin. They may be used alone or as a mixture of two or more. Particularly preferred are alumina and/or kaolin. The average pore diameter of the porous material is preferably within the range of 70 to 3000 Å, more preferably 80 to 2500 Å, most preferably 90 to 2000 Å. The average pore diameter of alumina is generally 50 to 500 Å, and that of kaolin is generally 100 to 3100 Å.

This support material can contain zeolite to further increase the hydrodealkylation activity.

Furthermore, alkali metals, alkaline earth metals, rare earth elements and the like can be contained as additives from the viewpoint of enhancing the thermal stability or selectivity of the catalyst.

This invention aims to satisfactorily carry out desulfurization, denitrogenation and other reactions in the hydrodealkylation step from the viewpoint of suppressing the poisoning of the catalyst in the alkylation step and in its turn realizing highly selective alkylation in high yields. For this reason, among the above catalysts, catalysts are preferred which can perform hydrodesulfurization of the stock oil simultaneously with the hydrodealkylation. More specifically, preferred catalysts are those capable of desulfurization such that sulfur of more than 70%, preferably more than 90%, still more preferably more than 95%, in the stock oil can be removed.

Accordingly, a preferred catalyst used in the 1st step comprises an oxide or sulfide of vanadium (V), molybdenum (Mo), or chromium (Cr) as the active metal component supported on a porous material that satisfies the above requirements. A catalyst comprising vanadium oxide $V_2O_x$ ($3.0 \leq x < 5.0$) is especially preferable, because this catalyst has especially high hydrodesulfurization actively even when coke is deposited on the catalyst.

The catalyst used in the 1st step may be in any form. When the reactor is of the fluidized bed type, substantially spherical particles are preferred from the viewpoint of good fluidity. The catalyst after use can be regenerated, for example, by a conventional regeneration method, for reutilization.

<REACTION CONDITIONS FOR THE 1ST STEP—TEMPERATURE>

The reaction temperature in the 1st step is preferably in the range of 450 to 700° C., more preferably in the range of 500 to 670° C. If the temperature is below 450° C, the hydrodealkylation conversion and the hydrodesulfurization rate will be too low, disadvantageously resulting in deteriorated yields and properties of naphthalene, methylnaphthalene and the like as the starting material in the 2nd step. On the other hand, a reaction temperature above 700° C. causes excessive hydrodealkylation and unnecessary side-reactions to produce undesirable by-products, posing problems such as deteriorated yields and properties of naphthalene, methylnaphthalene and the like as the starting material in the 2nd step and increased cost due to the necessity of a heat-resistant apparatus for coping with the high temperature reaction.

<REACTION CONDITIONS FOR THE 1ST STEP—PARTIAL PRESSURE OF HYDROGEN>

The partial pressure of hydrogen in the 1st step is preferably in the range of 1 to 50 kgf/cm$^2$, more preferably 2 to 40 kgf/cm$^2$, most preferably 3 to 30 kgf/cm$^2$. If the partial pressure of hydrogen is lower than 1 kgf/cm$^2$, the hydrodealkylation conversion and the hydrodesulfurization rate are too low and, at the same time, the deposition of coke on the catalyst is increased, resulting in deteriorated yields and properties of naphthalene, methylnaphthalene and other products as the starting material in the 2nd step.

On the other hand, a partial pressure of hydrogen exceeding 50 kgf/cm$^2$ poses a problem that hydrocracking due to hydrogenation of naphthalene ring occurs and consequently causes the generation of excess gas, resulting in deteriorated yields and properties of naphthalene, methylnaphthalene and other products as the starting material in the 2nd step and, at the same time, unnecessarily increased hydrogen consumption.

<REACTION CONDITIONS FOR THE 1ST STEP—CONTACT TIME>

The contact time in the 1st step is preferably in the range of 1 to 35 seconds, more preferably 2 to 30 seconds. If the contact time is less than 1 second, the hydrodealkylation conversion and the hydrodesulfurization rate are too low. This results in deteriorated yields and properties of naphthalene and methylnaphthalene and other products as the starting material in the 2nd step. On the other hand, a contact time exceeding 35 seconds causes excessive hydrodealkylation and unnecessary side-reactions to produce undesirable by-products, posing problems such as deteriorated yields and properties of naphthalene, methylnaphthalene and other products as the starting material in the 2nd step and increased cost due to the necessity of a larger reactor.

<SEPARATION AND RECOVERY OF PRODUCTS—OBTAINED IN THE 1ST STEP>

From the products obtained in the hydrodealkylation in the 1st step, naphthalene, β-methylnaphthalene, α-methylnaphthalene, and/or a mixture of β- and α-methylnaphthalenes are separated and recovered. This separation/recovery step may be performed, for example, by conventional distillation.

The 2nd Step of this Invention

<REACTOR>

The reactor used in the 2nd step may be of any type of a fixed bed, a moving bed, and a fluidized bed.

<STARTING MATERIAL TO BE FED>

The starting material in the 2nd step is naphthalene, β-methylnaphthalene, α-methylnaphthalene, and/or a mixture of β- and α-methylnaphthalene separated and recovered in the 1st step.

<ALKYLATION CATALYST>

Any catalyst may be used as the alkylation catalyst (the term "alkylation catalyst" used herein including "transalkylation catalyst") in the 2nd step, so far as the catalyst has alkylation activity. The alkylation catalyst may be any of liquid-phase alkylation catalysts and gas-phase alkylation catalysts. Since, however, the reaction in the 2nd step is typically carried out at a high temperature, it is preferable to use gas-phase alkylation catalysts rather than liquid-phase alkylation catalysts used at relatively low temperatures.

Typical examples of gas-phase alkylation catalysts usable herein include, but are not limited to, phosphoric acid supported on kieselguhr or silica, $BF_3/Al_2O_3$, zeolite, silica-alumina, $TiO_2$—$MoO_2$, $TiO_2$, $TiO_2$—$WO_3$, $MgO_2$, $MgO$—$MnO$—$Ce_2O_3$, $MgO$—$Al_2O_3$, and $Fe_2O_3$—$ZnO$. They may be used alone or as a mixture of two or more.

Particularly preferred catalysts are zeolites and silica-alumina. Zeolites usable herein include zeolite as X, Y, L, USY, mordenite, and ZSM-5 and β-zeolite. Used catalysts can be regenerated, for example, by a conventional regeneration method, for reutilization.

<ALKYLATING AGENT>

Typical examples of alkylating agents (the term "alkylating agent" used herein including "transalkylating agent") usable in the 2nd step include arenes, alkenes, alcohols, esters, ethers, and halogenated alkyls. Among them, any alkylating agent may be used in the 2nd step, so far as the alkylating agent can be used for alkylation, i.e., methylation, ethylation, or isopropylation. Examples of preferred arenes, that is, aromatic hydrocarbons, usable herein include alkylarenes, particularly those having at least one member selected from methyl, ethyl, and isopropyl groups. Alkylbenzenes and/or alkylnaphthalenes with two or more alkyl groups are more preferred.

Olefins, such as ethylene, propylene, butene, and isobutene, are preferred as the alkene with ethylene and propylene being more preferred.

Preferred alcohols are those having at least one member selected from methyl, ethyl, and isopropyl groups. More preferred are methyl alcohol, ethyl alcohol, and isopropyl alcohol.

Preferred esters and ethers are those having at least one member selected from methyl, ethyl, and isopropyl groups with dimethylcarbonate being more preferred.

Moreover, at least a portion of the residual fraction after the separation and recovery of dialkylnaphthalenes in the 3rd step can be used as the alkylating agent.

<REACTION CONDITIONS IN THE 2ND STEP—TEMPERATURE>

The reaction temperature in the 2nd step is preferably in the range of 200 to 550° C., more preferably in the range of 230 to 520° C., still more preferably in the range of 250 to 490° C. If the temperature is below 200° C., the alkylation may not proceed, resulting in lowered yields of dialkylnaphthalenes. On the other hand, a reaction temperature above 550° C. causes excessive alkylation and unnecessary side-reactions to produce undesirable by-products, posing problems such as deteriorated yields of dialkylnaphthalenes and increased cost due to the necessity of a heat-resistant apparatus for coping with the high temperature reaction.

In particular, in order to increase the yield of 2,6-dialkylnaphthalenes among the dialkylnaphthalenes, it is necessary to select proper temperature conditions. This is because the position of the alkyl group, in the naphthalene ring, introduced by the alkylation is greatly influenced by the reaction temperature.

<REACTION CONDITIONS IN THE 2ND STEP—PRESSURE>

The reaction pressure in the 2nd step is preferably in the range of 1 to 70 kg/cm$^2$, more preferably 2 to 50 kg/cm$^2$. If the reaction pressure is lower than 1 kg/cm$^2$, the deposition of coke on the catalyst is increased, resulting in accelerated reduction in catalytic activity. On the other hand, a reaction pressure exceeding 70 kg/cm$^2$ deteriorates process economics due to the necessity of very high pressurizing power and highly pressure-resistant materials.

The 3rd Step of this Invention

Dialkylnaphthalenes are separated and recovered from the alkylnaphthalenes obtained in the 2nd step. This separation is performed, for example, by conventional purification methods such as distillation, adsorption, and crystallization.

The 4th Step of this Invention

In this 4th step, at least a portion of the residual fraction after the separation and recovery of dialkylnaphthalenes, or of specific dialkylnaphthalenes, for example, 2,6-dialkylnaphthalenes, in the 3rd step is returned as at least a part of the stock oil in the 1st step and/or at least a part of the alkylating agent in the 2nd step to the corresponding step.

By this recycling, alkylnaphthalenes, especially dialkylnaphthalenes, can be produced efficiently. Return to the corresponding step may be carried out, for example, by conventional means or though a feed passage.

Brief Description of the Process Flow of the Invention

A general embodiment of the production of alkylnaphthalenes, particularly dialkylnaphthalenes, according to the process of the present invention will be explained with reference to the FIGURE. It should be noted that this process shown in the FIGURE merely illustrates an embodiment of the production process according to this invention, but are not intended to limit the scope of the invention.

<1ST STEP OF THE INVENTION>

A stock oil, together with hydrogen gas, is introduced through a stock oil feeder into a reactor 12. In the reactor 12, a hydrodealkylation catalyst is fluidized by the hydrogen gas to form a fluidized catalyst bed. In this reactor 12, the stock oil is hydrodealkylated in the presence of the hydrodealkylation catalyst to give a reaction product containing naphthalene and/or methylnaphthalenes as the target compounds.

The high temperature product flowing out of the top of the reactor 12 is introduced into a separator 13 comprising a gas-liquid separator and a distillation column. In the separator 13, the dealkylation product is cooled and separated from the hydrogen gas in the gas-liquid separator in the separator 13, and is then sent to the distillation column in the separator 13, where a fraction composed mainly of naphthalene and/or methylnaphthalenes is recovered.

The recovered fraction is forcibly transported by a pump 14 to the alkylation step as the 2nd step. If necessary, a plurality of distillation columns may be provided on a line between the stock oil feeder 11 and the reactor 12 and a line between the separator 13 and the reactor 21.

<2ND STEP OF THE INVENTION>

The fraction obtained in the 1st step is introduced into the reactor 21 in the 2nd step. A fixed bed of the alkylation catalyst is provided within the reactor 21. In this reactor 21, the fraction is alkylated with the alkylating agent fed from the feeder 22 in the presence of the alkylation catalyst to give an alkylation product containing dialkylnaphthalenes as the target compound. The product flowing from the bottom of the reactor 21 is transported to the separator 23.

<3RD STEP OF THE INVENTION>

The alkylation product sent to the separator 23 is introduced into the distillation column in the separator 23, and dialkylnaphthalenes as the target compounds are separated and sent to a receiver 24.

<4TH STEP OF THE INVENTION>

At least a portion of the residual fraction after the separation and recovery of the dialkylnaphthalenes in the separator 23 in the 3rd step is returned as at least a part of the stock oil in the 1st step and/or at least a part of the alkylating agent in the 2nd step from the separator 23 by a pump 31 to the corresponding step by pumps 32, 33, 34 and through feed lines or the like.

The steps described above enable alkylnaphthalenes, especially dialkylnaphthalenes, to be produced efficiently.

Examples

The following examples (including comparative examples) further illustrate this invention. It should be understood that the following examples are presented for facilitating the understanding of the invention and are not intended to limit the invention in any way.

EXAMPLE 1

[1ST STEP—HYDRODEALKYLATION STEP]

<REACTOR>

A fluidized bed reactor (inner diameter 2.8 cm) was used as the reactor.

<STOCK OIL>

A light cycle oil (boiling point range 200 to 270° C.) obtained from the catalytic cracking of petroleum was used as the stock oil. The stock oil was fed from a stock oil feeder to the hydrodealkylation reactor at a feed rate of 150 g/h. The concentration of naphthalene or alkylnaphthalenes in the stock oil was 38.4 wt %. The content of sulfur and the content of nitrogen in the stock oil were 600 ppm and 260 ppm, respectively. These values were obtained by the measurement with supercritical chromatography and elementary analysis.

<DEALKYLATION CATALYST>

The dealkylation catalyst comprised vanadium oxide (in the form of $V_2O_3$ or $V_2O_4$) supported as an active metal component (as vanadium (V) 3 wt %) on porous alumina particles with an average pore diameter of 168 Å. The reactor was packed with 500 cc of this catalyst.

This catalyst was prepared as follows. To 78 cc of an aqueous oxalic acid solution prepared by dissolving 15.0 g of oxalic acid in distilled water was dissolved 6.9 g of ammonium metavanadate per 100 g of porous alumina with pore volume 0.87 cc/g. Thus, an impregnation solution was obtained. The porous alumina particles were impregnated with the impregnation solution. The impregnated porous alumina particles were then dried at 95° C., and subjected to thermal decomposition and reduction with hydrogen to prepare the catalyst.

<REACTION CONDITIONS>

The hydrodealkylation was conducted in a hydrogen atmosphere under conditions of a temperature of 600° C., a partial pressure of hydrogen of 7 kg/cm², and a contact time of 7 seconds.

[1ST STEP—HYDRODEALKYLATION]

High temperature products flowing out of the upper outlet of the hydrodealkylation reactor was introduced into a hydrodealkylation product separator consisting of a gas-liquid separator and a distillation column. The hydrodealkylation product oil (98 g/h) was cooled in the gas-liquid separator to separate it from the hydrogen gas. A part of this hydrodealkylation product oil was fed to the distillation column, and each fraction of light oil, naphthalene, α-methylnaphthalene, and β-methylnaphthalene was recovered. A part of this β-methylnaphthalene was continuously pumped to the 2nd step (alkylation step) without cooling.

[2ND STEP—ALKYLATION STEP]

<REACTOR>

A fixed bed reactor (inner diameter 1.7 cm) was used as the alkylation reactor.

<FEED RATE>

β-Methylnaphthalene obtained in the 1st step was pumped into the alkylation reactor at a feed rate of 3.0 g/h.

<ALKYLATION CATALYST>

USY zeolite catalyst (Toso, HSZ-330HUD, $SiO_2/Al_2O_3$ molar ratio=6.18) was used as the alkylation catalyst. The reactor was packed with 6.0 g of this catalyst.

<ALKYLATING AGENT>

1,2,3,5-Tetramethylbenzene was used as an alkylating agent. The 1,2,3,5-tetramethylbenzene was fed from the alkylating agent feeder. The feed rate was adjusted so that the weight ratio of 1,2,3,5-tetramethylbenzene to β-methylnaphthalene was 1.0 wt/wt.

<REACTION CONDITIONS>

The transalkylation was conducted under conditions of a reaction temperature of 400° C., a total pressure of 0.2 kg/cm²G, and a contact time of 4.1 seconds.

[3RD STEP—SEPARATION AND RECOVERY OF DIALKYLNAPHTHALENE]

The transalkylation product was introduced from the alkylation reactor into a separator provided with a distillation column. From the distillation column, dimethylnaphthalenes was recovered as a product in a vessel. The dimethylnaphthalene isomers were analyzed by gas chromatography. The results are also shown below together with the reaction results.

[4TH STEP—RETURN OF ALKYLNAPHTHALENE OTHER THAN TARGET PRODUCT TO EACH STEP]

From the separator in the 3rd step, the by-product other than the target dimethylnaphthalenes was pumped out from the bottom of the separator. When use of the by-product as the hydrodealkylation stock oil was contemplated, the by-product was pumped into the hydrodealkylation reactor, while use of the by-product as the alkylating agent was contemplated, the by-product was pumped into the hydrodealkylation product separator and the alkylation reactor.

[RESULTS OF REACTION]

In the hydrodealkylation step, the yield of the product oil was 55.3 wt %, the concentrations of naphthalene, β-methylnaphthalene, and α-methylnaphthalene in the product oil were 26.2 wt %, 19.3 wt %, and 8.0 wt %, respectively, and the hydrodesulfurization rate was 98.9%. The β-methylnaphthalene obtained in this step was analyzed and found to have a purity of 98$^+$ wt %, a sulfur content of 45 ppm and a nitrogen content of 7 ppm. The results of transalkylation step.are shown in Tables 1 to 3 in comparison with Comparative Example 1.

Comparative Example 1

Commercially available β-methylnaphthalene (sulfur content 3000 ppm, nitrogen content 2100 ppm) separated from coal tar was provided as the stock oil. This stock oil was transalkylated. In this case, the alkylation reactor, catalyst, alkylating agent, reaction conditions, product separation method, and product analysis used were the same as those used in Example 1. The results are shown in Tables 1–3.

TABLE 1

Conversion and composition of product oil

|  | Example 1 | Comparative Example 1 |
|---|---|---|
| Conversion, % | 67.6 | 43.8 |
| Composition of product oil, mol % | | |
| Di-cyclic compounds | 54.9 | 52.8 |
| Mono-cyclic compounds | 44.3 | 46.5 |
| Unknowns | 0.8 | 0.6 |
| Total | 100.0 | 99.9 |

In this table, conversion denotes 100% –concentration of the feed compound in the product di-cyclic compounds (%). Di-cyclic compounds denote naphthalene +alkylnaphthalenes, and mono-cyclic compounds alkylbenzenes.

TABLE 2

Composition of product di-cyclic compounds

|  | Example 1 | Comparative Example 1 |
|---|---|---|
| Composition, mol % | | |
| Naphthalene | 8.0 | 4.6 |
| β-Methylnaphthalene | 32.4 | 56.2 |
| α-Methylnaphthalene | 13.7 | 23.9 |
| Dimethylnaphthalene | 32.5 | 13.6 |
| Trimethylnaphthalene | 11.5 | 1.7 |
| Tetramethylnaphthalene | 1.8 | 0.0 |
| Total | 99.9 | 100.0 |

TABLE 3

Composition of product dimethylnaphthalenes

|  | Example 1 | Comparative Example 1 |
|---|---|---|
| Composition, mol % | | |
| 2,6-Dimethylnaphthalene | 18.8 | 17.9 |
| 2,7-Dimethylnaphthalene | 17.2 | 18.5 |
| 1,3-+1,7-Dimethylnaphthalene | 31.5 | 31.6 |
| 1,6-Dimethylnaphthalene | 16.6 | 16.1 |
| 1,5-+1,4-+2,3-Dimethylnaphthalene | 12.4 | 11.9 |
| 1,2-+1,8-Dimethylnaphthalene | 3.5 | 4.0 |
| Total | 100.0 | 100.0 |

As is apparent from Tables 1 to 3, according to the process of this invention, as compared with the conventional process using the starting material obtained from coal tar, the conversion is higher, and the concentration of dialkylnaphthalenes in the product oil and the concentration of 2,6-dimethylnaphthalene in the product oil are higher. Namely, according to the process of this invention, the transalkylation can be efficiently performed without causing poisoning the transalkylating catalyst.

Example 2

[1ST STEP—HYDRODEALKYLATION STEP]

For a), the hydrodealkylation was conducted in the same manner as in Example 1.

For b), the hydrodealkylation was conducted in the same manner as in Example 1, except that the average pore diameter of the porous alumina particles used in the hydrodealkylation catalyst was 78 Å.

[2ND STEP—ALKYLATION STEP]

For both a) and b), the alkylation was conducted under the following conditions.

<REACTOR>

The same fixed bed reactor as used in Example 1 was used as the reactor.

<FEED RATE>

β-Methylnaphthalene produced in the 1st step was pumped into the reactor at a feed rate of 12.5 g/h.

<ALKYLATION CATALYST>

Amorphous silica-alumina (manufactured by Shokubai Kasei Kogyo, high alumina type, alumina content 30 wt %) was used as the catalyst. The reactor was packed with 32 cc of this catalyst.

<ALKYLATING AGENT>

Propylene was used as the alkylating agent. The propylene was fed from an alkylating agent feeder. The feed rate was adjusted so that the molar ratio of propylene to β-methylnaphthalene was 1.1 mol/mol.

<REACTION CONDITIONS>

The alkylation was conducted under conditions of a reaction temperature of 300° C., a total pressure of 3 kg/cm$^2$G, and a contact time of 35.5 seconds.

[3RD STEP—SEPARATION AND RECOVERY OF PRODUCT DIALKYLNAPHTHALENES]

The alkylation product was sent from the alkylation reactor to a separator provided with a distillation column. In the distillation column, monoisopropylmethylnaphthalene was distilled out and recovered as a product into a receiver. The obtained monoisopropylmethylnaphthalene was analyzed by gas chromatography using a polar column and NMR for isomer analysis.

[4TH STEP—RETURN OF RESIDUAL ALKYLNAPHTHALENE TO EACH STEP]

The residual alkylnaphthalenes after separation of monoisopropylmethylnaphthalene in the 3rd step were returned to each step in the same manner as in Example 1.

[RESULTS OF REACTION]

The results of the reaction in the hydrodealkylation step are shown in Table 4. The results of isopropylation of β-methylnaphthalene which has been produced in the presence of the hydrodealkylation catalyst with coke deposition of about 11 wt % in the hydrodealkylation step for both a) and b) are shown in Tables 5 to 7.

TABLE 4

Results of reaction in hydrodealkylation step

|  | a |  | b |  |
|---|---|---|---|---|
| Coke deposition on catalyst, wt % (weight of coke/weight of catalyst) | 3.7 | 10.4 | 5.6 | 11.8 |
| Hydrodesulfurization rate | 97.9 | 98.8 | 96.8 | 93.9 |
| Properties of β-methylnaphthalene |  |  |  |  |
| Purity | 98+ | 98+ | 98+ | 98+ |
| S content | 30 | 31 | 32 | 105 |
| N content | 5 | 5 | 6 | 9 |

TABLE 5

Conversion and composition of product oil

|  | a | b |
|---|---|---|
| Conversion, % | 60.3 | 48.7 |
| Composition of product oil, mol % |  |  |
| Isopropylnaphthalenes | 54.1 | 46.0 |
| β-Methylnaphthalene | 39.7 | 51.3 |
| Others | 6.2 | 2.7 |
| Total | 100.0 | 100.0 |

TABLE 6

Composition of product isopropylated methylnaphthalenes

|  | a | b |
|---|---|---|
| Composition, mol % |  |  |
| Isopropylmethylnaphthalenes | 74.2 | 68.9 |
| Diisopropylmethylnaphthalenes | 24.3 | 28.6 |
| Triisopropylmethylnaphthalenes | 1.5 | 2.5 |
| Tetraisopropylmethylnaphthalenes | 0.0 | 0.0 |
| Total | 100.0 | 100.0 |

TABLE 7

Composition of product isopropylated methylnaphthalenes

|  | a | b |
|---|---|---|
| Composition, mol % |  |  |
| 2,6-Isopropylmethylnaphthalene | 37.9 | 28.6 |
| 2,7-Isopropylmethylnaphthalene | 27.9 | 22.9 |
| 1,4-Isopropylmethylnaphthalene | 5.4 | 8.9 |
| 1,6-Isopropylmethylnaphthalene | 6.4 | 9.8 |
| 1,3-+2,3-Isopropylmethylnaphthalene | 8.9 | 13.1 |
| Other isopropylmethylnaphthalenes | 13.5 | 16.7 |
| Total | 100.0 | 100.0 |

It is understood that, according to the method of this invention, a higher conversion, a higher selectivity to monoisopropylmethylnaphthalene in the product isopropylated methylnaphthalenes and a higher selectivity to 2,6-isopropylmethylnaphthalene in monoisopropylmethylnaphthalene were obtained.

Namely, according to the process of this invention, the isopropylation can be efficiently performed.

For a) using alumina particles with larger average pore diameter in the hydrodealkylation step, more stable hydrodesulfurization activity was provided in the hydrodealkylation step even in the case of increased coke deposition on the catalyst, and the conversion and selectivity in the alkylation step were higher.

[EFFECTS OF THE INVENTION]

As can be understood from the examples, the process according to this invention can overcome problems of deactivation of catalyst and a reduction in conversion and selectivity in the reaction step and can produce high-purity dialkylnaphthalenes in high yields at low cost. In particular, this invention can easily and stably provide dialkylnaphthalenes, above all 2,6-dialkylnaphthalenes, very important compounds as precursors of monomers for synthesis of polyethylene naphthalates (PEN), which have received attention as engineering plastics required to have a high level of mechanical properties, heat-resistance, stability against chemicals, and electrical and optical properties, and, in addition, as precursors of monomers for synthesis of fully aromatic liquid crystal polymers which have recently drawn special attention. Thus, the invention can satisfy the requirements in related various industrial fields. This is as described in the paragraph of "SUMMARY OF THE INVENTION."

What is claimed is:

1. A process for producing dialkylnaphthalenes, comprising (1), (2), (3), and (4):
   (1) catalytically hydrodealkylating a stock oil containing an amount of naphthalene and/or alkylnaphthalenes, separating a product oil from a product gas, and separating and recovering a fraction composed mainly of naphthalene and/or methylnaphthalene from the product oil; wherein the stock oil is a light cycle oil fraction of catalytic cracking of petroleum and has a boiling point in the range of 210 to 280° C.; and the hydrodealkylation is carried out in the presence of a hydrodealkylation catalyst comprising a carrier and an active metal component supported on the carrier, the active metal component comprising at least one metal selected from the group consisting of vanadium (V), molybdenum (Mo), chromium (Cr), cobalt (Co), nickel (Ni), platinum (Pt), rhodium (Rh), and iridium (Ir), and/or an oxide or sulfide of said metals, said carrier supporting the active metal component is a material having a porous structure, and comprises at least one member selected from the group consisting of alumina, silica, silica alumina, and kaolin; and said porous material has an average pore diameter in the range of 70 to 3000 Å;
   (2) catalytically alkylating or catalytically transalkylating the fraction, recovered in (1), composed mainly of naphthalene and/or methylnaphthalene directly without pretreatment for purification, with an alkylating agent or a transalkylating agent to prepare alkylnaphthalenes;
   (3) separating and recovering dialkylnaphthalenes from the alkylnaphthalenes obtained in (2); and
   (4) returning at least a part of the residual fraction, after the separation and recovery of dialkylnaphthalenes in (3), as at least a part of the stock oil in (1) and/or at least a part of the alkylating agent or transalkylating agent in (2) to the corresponding step.

2. The process according to claim 1, wherein the active metal component is at least one member selected from the group consisting of vanadium (V), molybdenum (Mo), and chromium (Cr) and/or an oxide or sulfide of said metals.

3. The process according to claim 1, wherein the active metal component is an oxide of vanadium (v) $V_2O_x$ wherein x is 3.0 to less than 5.0.

4. The process according to claim 1, wherein the concentration of the active metal component in terms of the metal is in the range of 0.1 to 30 wt %.

5. The process according to claim 1, wherein the porous material comprises alumina and/or kaolin.

6. The process according to claim 1, wherein the catalyst further comprises at least one member selected from the group consisting of zeolite, alkali metals, alkaline earth metals, and rare earth metals.

7. The process according to claim 1, wherein, in (1), the hydrodealkylation is carried out under conditions of temperature 450 to 700° C., partial pressure of hydrogen 1 to 50 kg/cm$^2$, and contact time 1 to 35 seconds.

8. The process according to claim 1, wherein said porous material has an average pore diameter of 100 to 3000 Å.

9. A process for producing dialkylnaphthalenes, comprising (1), (2), (3), and (4):

(1) catalytically hydrodealkylating, hydrodesulfurizing and hydrodenitrogenating a stock oil containing an amount of naphthalene and/or alkylnaphthalenes, separating a product oil from a product gas, and separating and recovering a fraction composed mainly of naphthalene and/or methylnaphthalene from the product oil; wherein the stock oil is a light cycle oil fraction of catalytic cracking of petroleum and has a boiling point in the range of 210 to 280° C.; and the hydrodealkylation is carried out in the presence of a hydrodealkylation catalyst comprising a carrier and an active metal component supported on the carrier, the active metal component comprising at least one metal selected from the group consisting of vanadium (V), molybdenum (Mo), chromium (Cr), cobalt (Co), nickel (Ni), platinum (Pt), rhodium (Rh), and iridium (Ir), and/or an oxide or sulfide of said metals, said carrier supporting the active metal component is a material having a porous structure, and comprises at least one member selected from the group consisting of alumina, silica, silica alumina, and kaolin; and said porous material has an average pore diameter in the range of 70 to 3000 Å;

(2) catalytically alkylating or catalytically transalkylating the fraction, recovered in (1), composed mainly of naphthalene and/or methylnaphthalene directly without pretreatment for purification, with an alkylating agent or a transalkylating agent to prepare alkylnaphthalenes;

(3) separating and recovering dialkylnaphthalenes from the alkylnaphthalenes obtained in (2); and (4) returning at least a part of the residual fraction, after the separation and recovery of dialkylnaphthalenes in (3), as at least a part of the stock oil in (1) and/or at least a part of the alkylating agent or transalkylating agent in (2) to the corresponding step.

* * * * *